United States Patent [19]

Bergstrom et al.

[11] Patent Number: 5,438,131
[45] Date of Patent: Aug. 1, 1995

[54] 3-NITROPYRROLE NUCLEOSIDE

[76] Inventors: Donald E. Bergstrom, 903 Fifth St., West Lafayette, Ind. 47906; Philip C. Andrews; Ruthann Nichols, both of 108 South Revena Blvd., Ann Arbor, Mich. 48103; Peiming Zhang, 2429-1A N. Armstrong, West Lafayette, Ind. 47906

[21] Appl. No.: 946,971

[22] Filed: Sep. 16, 1992

[51] Int. Cl.$^6$ .................. C07H 15/12; C07H 17/00; C07H 5/04; C07H 19/00
[52] U.S. Cl. .................. 536/28.6; 536/18.7; 536/22.1; 536/26.1; 536/26.9; 536/28.7; 536/28.8; 536/28.9
[58] Field of Search .................. 536/18.7, 22.1, 26.1, 536/26.9, 28.6, 28.7, 28.8, 28.9

[56] References Cited

U.S. PATENT DOCUMENTS

| | | | |
|---|---|---|---|
| Re. 29,835 | 11/1978 | Witkowski et al. | 536/26.9 |
| 3,798,209 | 3/1974 | Witkowski et al. | 536/26.9 |
| 3,984,396 | 10/1976 | Witkowski et al. | 536/26.9 |
| 4,531,001 | 7/1985 | Robins et al. | 536/26.9 |

FOREIGN PATENT DOCUMENTS

| | | | |
|---|---|---|---|
| 130596 | 7/1985 | Japan | 536/26.9 |
| 1029393 | 1/1989 | Japan | 536/28.6 |

OTHER PUBLICATIONS

D. Bergstrom, "In Search of the Universal Nucleic Acid Base," Department of Health and Human Services Public Health Service Grant Application (1990).
D. Bergstrom, "An Efficient Route to C-4 Linked Imidazole Nucleosides: Synthesis of 2-Carbamoyl-4-(2'-Deoxy-β-D-Ribofuranosyl)Imidazole," 32 *Tetrahedron Letters* 6485-6488 (1991).
U. B. Gyllensten, "PCR and DNA Sequencing," 7 *BioTechniques* 700-708 (1989).
F. Sanger, S. Nicklen and A. R. Coulson, "DNA Sequencing With Chain-Terminating Inhibitors," 74 *Proc. Natl. Acad. Sci. USA* 5463-5467 (1977).
F. Sanger, "Determination of Nucleotide Sequences in DNA," 214 *Science* 1205-1210 (1981).
A. Williamson and E. Rybicki, "Antisense Nucleic Acid Technology and Gene Regulation," 87 *South African Journal of Science* 478-480 (1991).
S. T. Crooke, "Therapeutic Applications of Oligonucleotides," 10 *Bio/Technology* 882-886 (1992).
P. D. Cook, "Medicinal Chemistry of Antisense

*Primary Examiner*—Douglas W. Robinson
*Assistant Examiner*—L. Blaine Lankford
*Attorney, Agent, or Firm*—Woodard, Emhardt, Naughton, Moriarty & McNett

[57] ABSTRACT

Oligonucleotides having at least ten nucleosides, at least two of which are selected from the group consisting of A, T, C and G, and at least one nucleoside being a universal nucleoside of the formula:

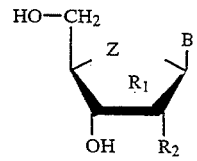

wherein:
each $R_n$ is H, OH, F or $OCH_3$;
Z is a member of the group consisting of O, S and $CH_2$; and
B is a five-membered, heterocyclic base having at least two double bonds, and further having an electron withdrawing group bonded thereto, said base with electron withdrawing group being represented by the formula:

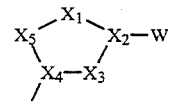

wherein:
said base with electron withdrawing group is bonded at $X_4$ to the sugar portion of the nucleoside;
$X_1$, $X_3$ and $X_5$ are each members of the group consisting of N, O, C, S and Se;
$X_2$ and $X_4$ are each members of the group consisting of N and C; and
W is a member of the group consisting of F, Cl, Br, I, O, S, OH, SH, $NH_2$, $NO_2$, C(O)H, C(O)NHOH, C(S)NHOH, NO, $C(NOCH_3)NH_2$, $OCH_3$, $SCH_3$, $SeCH_3$, $ONH_2$, $NHOCH_3$, $N_3$, CN, $C(O)NH_2$, $C(NOH)NH_2$, $CSNH_2$ and $CO_2H$.

1 Claim, 5 Drawing Sheets

OTHER PUBLICATIONS

Oligonucleotides-Future Opportunities," 6 *Anti-Cancer Drug Design* 585-607 (1991).

L. Leserman, G. Degols, P. Machy, J. Leonetti, N. Mechti and B. Leblue, "Targeting and Intracellular Delivery of Antisense Oligonucleotides Interfering With Oncogene Expression," *Prospects for Antisense Nucleic Acid Therapy of Cancer and AIDS* 25-33 (1991).

Y. Takahashi, K. Kato, Y. Hayashizaki, T. Wakabayashi, E. Ohtsuka, S. Matsuki, M. Ikehara and K. Matsubara, "Molecular Cloning of the Human Cholecystokinin Gene by Use of a Synthetic Probe Containing Deoxyinosine," 82 *Proc. Natl. Acad. Sci. USA* 1931-1935 (1985).

E. Ohtsuka, S. Matsuki, M. Ikehara, Y. Takahashi and K. Matsubara, "An Alternative Approach to Deoxyoligonucleotides as Hybridization Probes by Insertion of Deoxyinosine at Ambiguous Codon Positions," 260 *The Journal of Biological Chemistry* 2605-2608 (1985).

W. M. McShan, R. D. Rossen, A. H. Laughter, J. Trial, D. J. Kessler, J. G. Zendegui, M. E. Hogan and F. M. Orson, "Inhibition of Transcription of HIV-1 in Infected Human Cells by Oligodeoxynucleotides Designed to Form DNA Triple Helices," 267 *The Journal of Biological Chemistry* 5712-5721 (1992).

C. Helene, "the Anti-Gene Strategy: Control of Gene Expression by Triplex-Forming-Oligonucleotides," 6 *Anti-Cancer Drug Design* 569-584 (1991).

S. L. Young, S. H. Krawczyk, M. D. Matteucci and J. J. Toole, "Triple Helix Formation Inhibits Transcription Elongation *In Vitro*," 88 *Proc. Natl. Acad. Sci. USA* 10023-10026 (1991)

A. S. Moffat, "Triplex DNA Finally Comes of Age," 252 *Science* 1374-1375 (1991).

M. I. Dawson, A. N. Jina, S. Torkelson, S. Rhee, M. Moore, D. A. Zarling and P. D. Hobbs, "Synthesis and Characterization of a Ribavirin-3',5'-Phosphate Pentadecamer Homoribopolymer Bearing a 5'-Amino Tether Group and a 3'-Thymidine," 18 *Nucleic Acids Research* 1099-1102 (1990).

S. Pochet and R. D'Ari, "Synthesis and Enzymatic Polymerisation of 5-Amino-1-(2'-Deoxy-$\beta$-D-Ribofuranosyl)Imidazole-4-Carboxamide-5'-Triphosphate," 18 *Nucleic Acids Research* 7127-7131 (1990).

T. A. Millican, G. A. Mock, M. A. Chauncey, T. P. Patel, M. A. W. Eaton, J. Gunning, S. D. Cutbush, S. Neidle and J. Mann, "Synthesis and Biophysical Studies of Short Oligodeoxynucleotides With Novel Modifications: A Possible Approach to the Problem of Mixed Base Oligodeoxynucleotide Synthesis," 12 *Nucleic Acids Research* 7435-7453 (1984).

F. Seela and K. Kaiser, "Phosphoramidites of Base-Modified 2'-Deoxyinosine Isosteres and Solid-Phase Synthesis of d(GCI CGC) Oligomers Containing an Ambiguous Base," 14 *Nucleic Acids Research* 1825-1845 (1986).

P. K. T. Lin and D. M. Brown, "Synthesis and Duplex Stability of Oligonucleotides Containing Cytosine-Thymine Analogues," 17 *Nucleic Acids Research* 10373-10383 (1989).

P. Francois, D. Perilleux, Y. Kempener and E. Sonveaux, "Flexible Aglycone Residues in Duplex DNA," 31 *Tetrahedron Letters* 6347-6350 (1990).

J. F. Habener, C. D. Vo, D. B. Le, G. P. Gryan, L. Ercolani and A. H.-J. Wang, "5-Fluorodeoxyuridine as an Alternative to the Synthesis of Mixed Hybridization Probes for the Detection of Specific Gene Sequences," 85 *Proc. Natl. Acad. Sci. USA* 1735-1739 (1988).

K. Ramasamy, R. K. Robins and G. R. Revankar, "Total Synthesis of 2'-Deoxytoyocamycin, 2'-Deoxysangivamycin and Related 7-$\beta$-D-Arabinofuranosylpyrrolo(2,3-d) Pyrimidines *Via* Ring Closure of Pyrrole Precursors Prepared by the Stereospecific Sodium Salt Glycosylation Procedure," 42 *Tetrahedron* 5869-5878 (1986).

(List continued on next page.)

OTHER PUBLICATIONS

K. Ramasamy, R. K. Robins and G. R. Revankar, "Synthesis of Brunfelsamidine Ribonucleoside and Certain Related Compounds by the Sterospecific Sodium Salt Glycosylation Procedure," 7(3) *Neucleosides & Nucleotides* 385–392 (1988).

J. T. Witkowski, M. Fuertes, P. D. Cook and R. K. Robins, "Necleosides of 1,2,4–Triazole–3–Carboxamide: Synthesis of Certain Pentofuranosyl, Deoxypento–furanosyl and Pentopyranosyl 1,2,4–Triazoles," 2(1) *Journal of Carbohydrates•Nucleosides•Nucleotides* 1–36 (1975).

O. Makabe, H. Suzuki and S. Umezawa, "Syntheses of D–Arabinofuranosyl and 2'–Deoxy–D–Ribofuranosyl 1,2,3–Triazolecarboxamides," 50 *Bulletin of the Chemical Society of Japan* 2689–2693 (1977).

T. Huynh–Dinh and J. Igolen, "Synthesis of C–Nucleosides. Part 14. 5(3)–Glycosyl–1,2,4–Triazole–3(5)–Carboxamides as Analogues of Ribavirin," *J. C. S. Perkin I* 761–764 (1977).

Abstract 102:77265x, 102 *16–Fermentations* 469 (1985).
Abstract 84766a, 78 *Chemical Abstracts* 472 (1973).

(2.1)

(2.2)

(3.1)

(3.2)

(4.1)

(4.2)

(4.3)

(5.1)

(5.2)

(5.3)

(5.4)

3-NITROPYRROLE NUCLEOSIDE

BACKGROUND TO THE INVENTION

This invention was made with U.S. Government support under Grant #R01 GM45551 awarded by the National Institute of Health. The U.S. Government has certain rights in the invention. The invention was also developed with support from Purdue University, the University of Michigan and the Walther Cancer Institute.

FIELD OF THE INVENTION

The present invention relates generally to oligonucleotides, and more particularly to oligonucleotides having universal nucleosides included therein.

The chemical synthesis of oligonucleotides has had tremendous biological application over the past several decades. The simultaneous development of rapid and efficient methods of synthesis, together with advances in molecular biology techniques, has led to an increasing demand for synthetic oligonucleotides. Oligonucleotides can serve a multitude of purposes, including use as hybridization probes for DNA isolation, as primers in the enzymatic amplification of DNA, as mutagens for site-directed DNA alterations, and as sequencing primers.

A major use of synthetic oligonucleotides is the identification of naturally-occurring DNA sequences. The efficient isolation of specific DNA sequences depends to a great extent on the ability to accurately identify the DNA or RNA sequence of interest. When amino acid sequence information is available, it is possible to approximately deduce the nucleotide sequence and then synthesize an oligonucleotide that can be used to identify clones containing the desire sequence. This approach has been used very successful and is one of the most widely used methods for identifying specific DNA or RNA sequences.

Due to redundancy in the genetic code, it is almost always impossible to precisely predict a unique nucleotide sequence from an amino acid sequence. Mixtures of oligonucleotides that take this redundancy into account must be synthesized and used for screening potential DNA or RNA candidates. However, the potential ambiguities or mismatches present in the sequences of a highly degenerate oligonucleotide mixture can result in the identification of colonies which contain sequences that are unrelated to the DNA or RNA sequence of interest. This may be partially overcome by modifying the stringency of the hybridization conditions. An additional problem occurs if the oligonucleotide mixture contains a large number of sequences. In that case, the correct sequence may be diluted to the point that the mixture becomes ineffective.

Unfortunately, there is often no alternative to the use of a complex mixture of oligonucleotides. The design of longer, unique oligonucleotides making use of species-specific codon frequencies to increase the probabilities of correct base pairing is not always an option. Frequently the use of protein sequence information to screen DNA or RNA sequences is seriously limited due to either high degeneracy or incomplete or uncertain protein sequence information.

One solution to the problem has been to seek bases that would hybridize equally to more than one nucleic acid base and hence decrease the number of partially redundant probes required. This has led to the concept of a "universal base," a modified nucleic acid base that could base-pair with ally of the common bases: deoxyadenosine (A), deoxythymidine (T), deoxycytidine (C) and deoxyguanosine (G). Reference herein to A, C, G and T is intended to additionally encompass the RNA analogs thereto, including uridine (U) as the analog to T. The use of a universal base should reduce the degeneracy to 1 and still preserve the uniqueness of the probe. Successful development of a universal base could greatly reduce the element of risk and enhance success in screening DNA libraries.

A variety of compounds have been investigated as universal bases and examples of such compounds are shown in FIG. 1. For example, Millican et al. proposed the use of either 1,2-dideoxyribofuranose or 1,2-dideoxy-1(C)-phenylribofuranose as a universal base in a paper published in 1984. Ikehara and Inaoka synthesized the deoxyriboside of benzimidazole, and suggested its use in oligonucleotides.

Hypoxanthine, xanthine and guanine deoxyribonucleosides have been evaluated for their ability to hybridize to each of the four DNA bases in nonadecamers. The ninth base from the 5' end was modified in the sequence 5'-CGATGTTAYTACATGAGAC-3' and binding to the four sequences 5'-GTCTCATGTAN-TAACATCG-3' (N=A, C, G or T) was determined. Each of the substitutions destabilized the duplex relative to a control in which a G-C base pair occurred at this position.

Although it has been widely promoted, deoxyinosine is not as discriminating in forming base pairs as is required for many applications and has not met widespread acceptance. Since its introduction in 1985 as a "universal base" there have been some reports of its successful use in DNA probes, however many more studies have been published using oligonucleotide mixtures than using deoxyinosine—suggesting that the need for a truly universal base remains.

The feasibility of using 5-fluorodeoxyuridine (F) as a base analog has been examined in synthetic oligonucleotides. The A-F base pair is actually more stable than an A-T base pair and increases the $T_m$ 1° C. above an A-T pair. A G-F base pair is essentially neutral. Unfortunately, the application of 5-fluoracil as a universal base is limited to pairing with A and G.

The introduction of a universal base would have numerous advantages. As has been stated, the total number of sequences in a degenerate oligonucleotide mixture would be reduced. This would increase the effective specific activity of the correct sequence by exactly the amount due to the reduction in degeneracy. One of the limiting factors in the use of highly degenerate oligonucleotide mixtures as probes for screening DNA or RNA sequences is the reduction in effective specific activity of the correct probe sequence in the large population of incorrect oligonucleotide sequences.

Second, a universal base would promote a uniform distribution of oligonucleotides. For example, when all four bases are incorporated into an oligonucleotide during chemical synthesis, all four bases are not equally represented due to different rates of degradation and to different degrees of phosphoramidite reactivity. This may cause under-representation of certain sequences in an oligonucleotide mixture.

A need therefore exists for oligonucleotides having universal bases at potentially degenerate positions so that the oligonucleotide will bond to ambiguous DNA or RNA sequences. The present invention addresses that need.

SUMMARY OF THE INVENTION

Briefly describing the present invention, there are provided novel oligonucleotides comprising at least ten nucleosides, wherein at least two different nucleosides are selected from the group consisting of A, T, C and G, and wherein at least one nucleoside is a universal nucleoside of the formula:

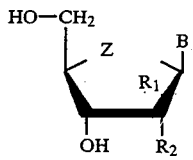

wherein in the first cyclic structure illustrated above:
each $R_n$ is H, OH F or $OCH_3$;
Z is a member of the group consisting of O, S and $CH_2$; and
B is a second cyclic structure comprising a five-membered, cyclic base having at least two double bonds in one of its possible tautomeric forms, and further having an electron withdrawing group bonded thereto, said base with electron withdrawing group being represented by the formula:

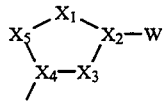

wherein:
said base with electron withdrawing group is bonded at $X_4$ to the second cyclic structure of the nucleoside;
$X_1$, $X_3$ and $X_5$ are each members of the group consisting of N, O, C, S and Se;
$X_2$ and $X_4$ are each members of the group consisting of N and C; and
W is a member of the group consisting of F, Cl, Br, I, O, S, OH, SH, $NH_2$, $NO_2$, C(O)H, C(O)NHOH, C(S)NHOH, NO, $C(NOCH_3)NH_2$, $OCH_3$, $SCH_3$, $SeCH_3$, $ONH_2$, $NHOCH_3$, $N_3$, CN, $C(O)NH_2$, $C(NOH)NH_2$, $CSNH_2$ and $CO_2H$.

One object of the present invention is to provide oligonucleotides which include universal nucleosides at degenerate positions.

Further objects and advantages of the present invention will be apparent from the following description.

DESCRIPTION OF THE PREFERRED EMBODIMENT

For the purposes of promoting an understanding of the principles of the invention, reference will now be made to preferred embodiments and specific language will be used to describe the same. It will nevertheless be understood that no limitation of the scope of the invention is thereby intended, such alterations and further modifications in the illustrated aspects of the invention, and such further applications of the principles of the invention as illustrated herein being contemplated as would normally occur to one skilled in the art to which the invention relates.

One aspect of the present invention relates to oligonucleotides comprising at least ten nucleosides, at least two of which are selected from the group consisting of A, T, C and G, and at least one nucleoside being a universal nucleoside. The incorporation of one or more universal nucleosides into the oligomer makes bonding to unknown bases possible and allows the oligonucleotide to match ambiguous or unknown nucleic acid sequences. In one preferred aspect, all of the common DNA nucleosides—deoxyadenosine (A), thymidine (T), deoxycytidine (C) and deoxyguanosine (G)—are combined with at least several of the universal nucleosides to make an oligonucleotide having at least 10 nucleosides therein.

Considering first the universal nucleoside portion of the present invention, the preferred nucleosides of the present invention include a first (sugar) portion and a second (base) portion. The first portion of the nucleoside can be represented by the formula:

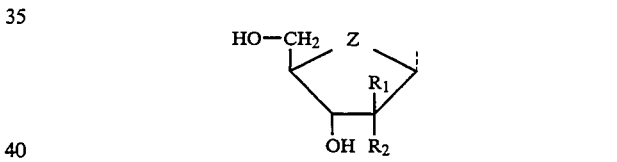

wherein each $R_n$ is H, OH, F or $OCH_3$, and Z is a member of the group consisting of O, S and $CH_2$.

Figure 1:
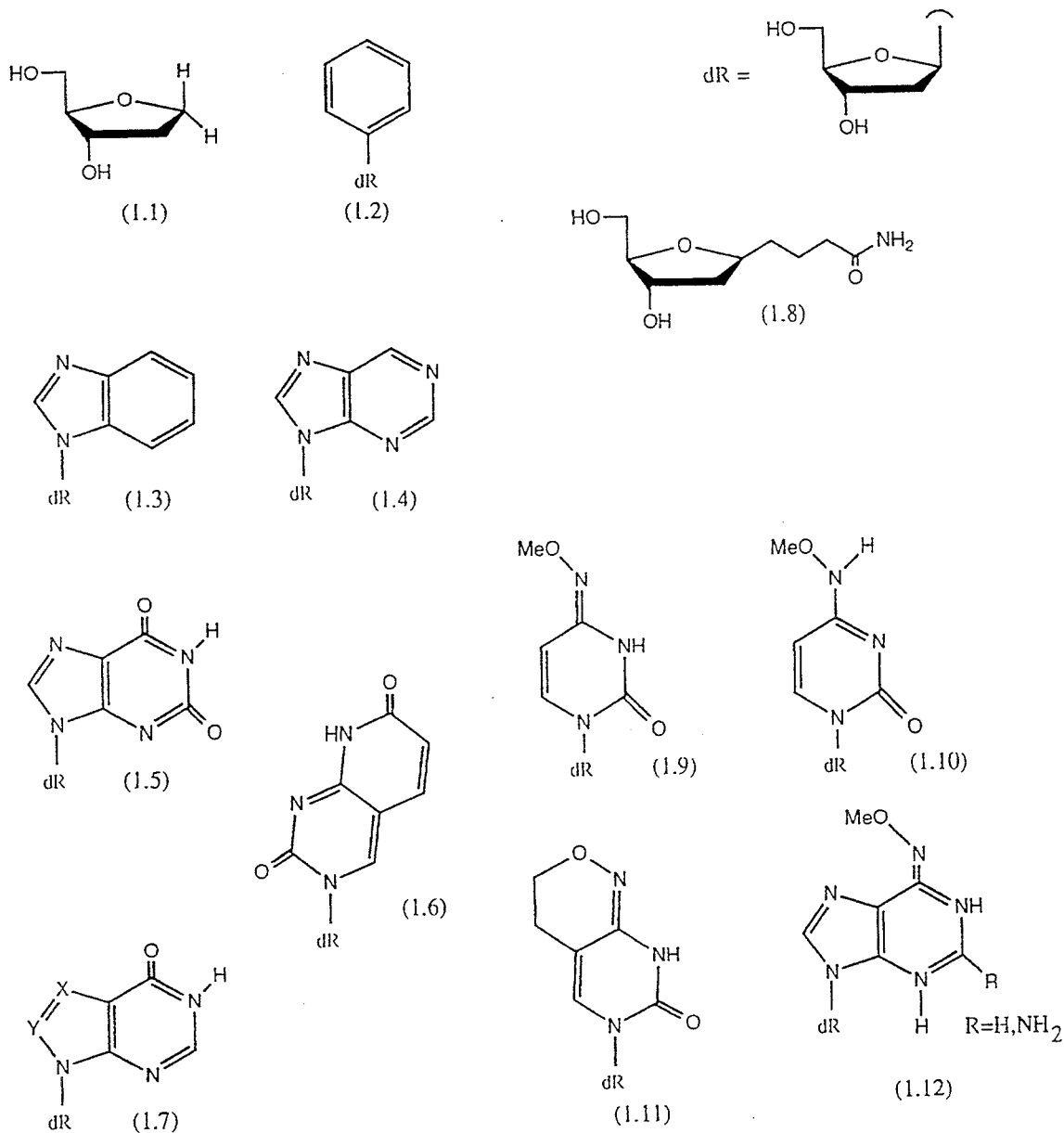
FIG. 1 shows various compounds which have been proposed as universal nucleosides in the prior ark.
Figure 2:
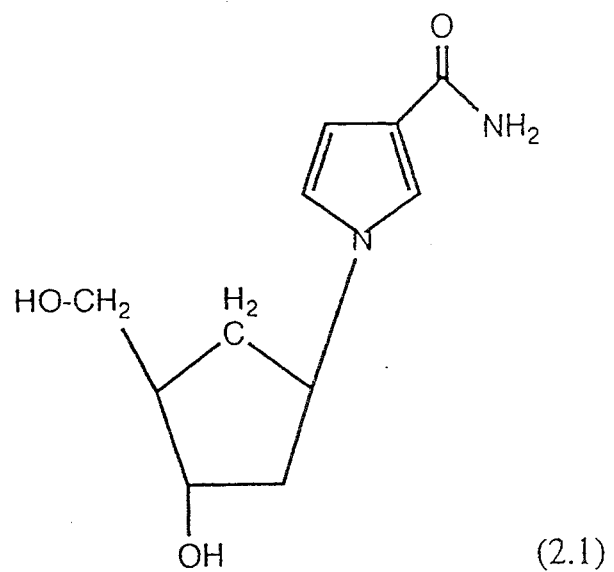
FIG. 2 shows nucleosides in which the cyclic oxygen of the sugar portion is replaced with S or $CH_2$.
Figure 2:
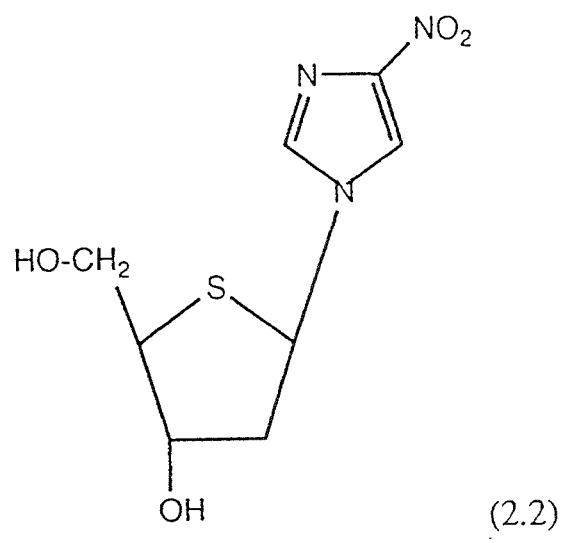

Most commonly, the first (sugar) portion will be D-deoxyribose or D-ribose as found in naturally occurring ribonucleosides and deoxyribonucleosides. The Z atom of the above formula will be O in these preferred cases. Alternatively, the oxygen of this cyclic structure may be replaced by either S or $CH_2$ without unreasonably affecting the performance of the nucleoside in some applications. Examples of nucleosides having a first "sugar" portion which is substituted with S or $CH_2$ are shown in FIG. 2; additional examples of such compounds may be developed by those skilled in the art without undue experimentation.

A variety of substituents may be included at $R_1$ and/or $R_2$. In particular, both $R_1$ and $R_2$ may be H as in the case of D-deoxyribose. If one of those substituents is H and the other is OH the first (sugar) portion may be D-ribose as in naturally-occurring ribonucleosides. Alternatively, either or both of $R_1$ and $R_2$ may be substituted with F or $OCH_3$. The use of fluorine substituted nucleosides has been suggested by the prior art as in, for example, 2'-fluoro-2'-deoxyadenosine, which was incorporated into oligonucleotides by M. Ikehara and coworkers (Ikehara, 21 *Heterocycles* 75, 1984).

The second (base) portion "B" of the universal nucleosides is preferably a five-membered, heterocyclic base having at least two double bonds in one of its possible tautomeric forms, and further having an electron withdrawing group bonded thereto. Preferred base portions are represented by the formula:

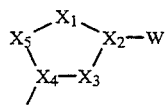

Figure 3:
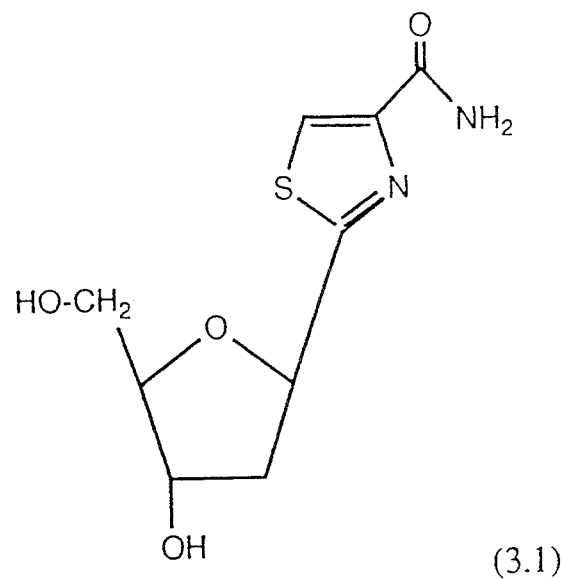
FIG. 3 shows nucleosides in which the base portion is a heterocycle including O, S or Se.
Figure 3:
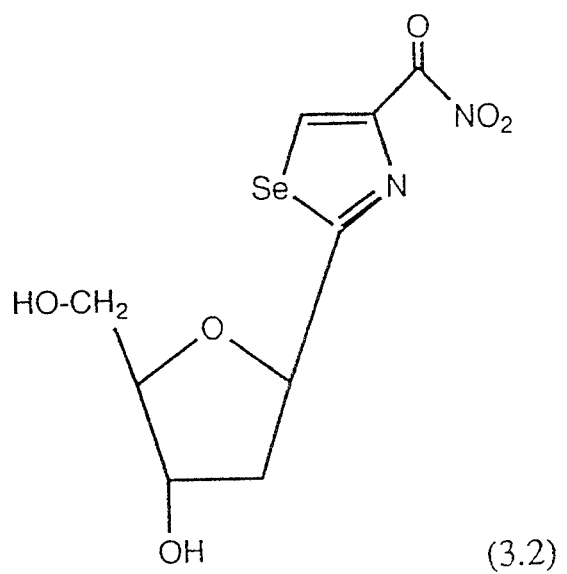

As was mentioned above, $X_1$, $X_3$ and $X_5$ are each members of the group consisting of C, N, O, S and Se. In the universal nucleosides preferred in testing to date, $X_1$, $X_3$ and $X_5$ are either C or N, with the most preferred compounds including at least one N. Alternative nucleosides including O, S or Se are shown in FIG. 3; additional alternatives may be prepared by one skilled in the art without undue experimentation.

As was stated above, $X_2$ and $X_4$ are each preferably members of the group consisting of N and C. In the nucleosides most preferred in testing to date at least one of these two atoms is N, although the exact location of the nitrogen may vary according to the particular application.

lit is to be appreciated that there are some limitations as to which atoms can be located at $X_1$, $X_2$, $X_3$ and $X_5$. In particular, when $X_4 = N$ and $X_4$ is the site of the glycosidic bond, then $X_1$, $X_3$ and $X_5$ can only be C or N, and $X_2$ must be C. O, S or Se can be tolorated at $X_1$, $X_3$ and $X_5$ only when $X_4 = C$, and even in that case there can be no more than one of these atoms (O, S and Se) in the five-membered heterocyclic ring.

Figure 4:
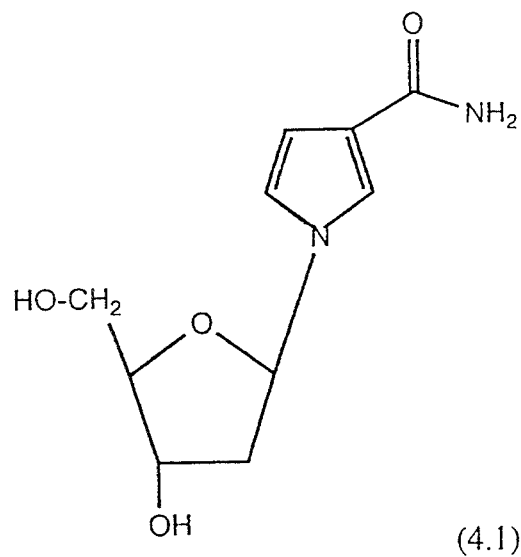
FIG. 4 shows nucleosides in which the base portion is a pyrrole, diazole or triazole derivative.
Figure 4:
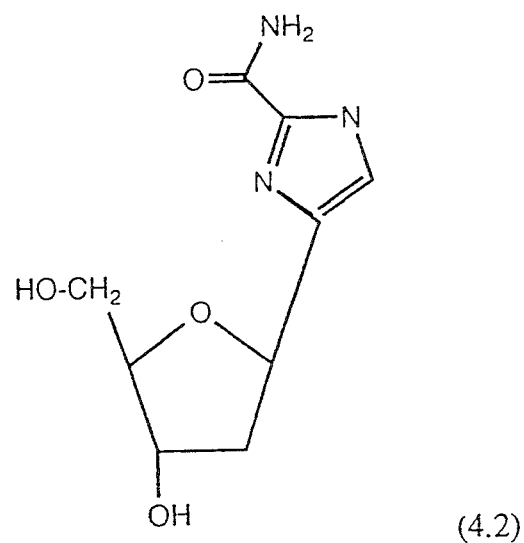
Figure 4:
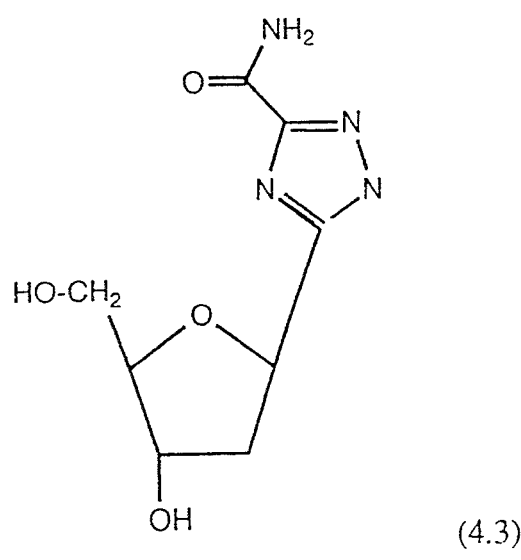

When N is included in the nucleoside, the base may be, for example, a pyrrole, diazole or triazole. Examples of such nucleosides are shown ill FIG. 4, and can be prepared by one skilled in the art without undue experimentation.

The electron withdrawing group W is a member of the group consisting of F, Cl, Br, I, O, S, OH, SH, $NH_2$, $NO_2$, C(O)H, C(O)NHOH, C(S)NHOH, NO, $C(NOCH_3)NH_2$, $OCH_3$, $SCH_3$, $SeCH_3$, $ONH_2$, $NHOCH_3$, $N_3$, CN, $C(O)NH_2$, $C(NOH)NH_2$, $CSNH_2$ and $CO_2H$. $NO_2$ bas been especially effective in experiments to date, and is particularly preferred for Sanger sequencing. $C(O)NH_2$ has also been particularly effective in certain applications.

A number of structural features of the preferred base portions should be mentioned. First, it is to be appreciated that the electron withdrawing group is bonded to the remainder of the base portion only at $X_2$. In some unsatisfactory prior art nucleosides, such as deoxyinosine, the electron withdrawing group bonds to the remainder of the base portion at both $X_2$ and $X_3$—which limits the ability of the base to assume a position necessary to optimize both hydrogen bonding and base stacking.

Adding substituents at $X_1$, $X_3$ or $X_5$ may be effective in some cases, although any substituents added at those positions must be small enough to avoid steric interference and must not prevent effective base stacking and bonding interactions. Small substituents which do not interfere with the coplanarity of the extended ring system are preferred. $X_1$, $X_3$ or $X_5$ should be C if a substituent is added to that atom. Nucleosides in which such substituents are included at $X_1$, $X_3$ or $X_5$ are to be considered equivalent to the specifically disclosed nucleosides.

Preferably, the base-with-electron withdrawing group comprises an extended $\pi$ system which favors base stacking interactions. Specifically, the preferred electron withdrawing groups enhance base stacking through interaction with adjacent pyrimidine and purine ring systems in a polynucleohide double helix.

The universal nucleosides of the present invention accordingly preferably possess the following chemical and structural properties:

1. One or more donor or acceptor sites for hydrogen bonding to A, C, G or T.
2. Planar aromatic $\pi$ system capable of stacking interactions with A, C, G and T in duplex or triplex nucleic acids.
3. The molecule is sterically accommodated within duplex or triplex nucleic acid, while at the same time maintaining both base stacking and hydrogen bonding interactions.
4. At least one of the following derivatives of the universal nucleoside is chemically accessible and stable: a phosphoramidite substituted by a protecting group such as cyanoethyl; H-phosphonate; a phosphodiester in which one of the phosphorus substituents is a protecting group such as O-chlorophenyl; or a phosphide triester in which two of the substituents can function as either transient protecting groups or leaving groups for phosphorus ester formation.
5. The universal nucleoside, once incorporated into oligonucleotide under construction, is completely stable to the reagents and conditions of oligonucleotide synthesis as well as stable to oxygen, light and water.

The synthesis of oligonucleotides from their nucleosidal components is accomplished in a straightforward manner using standard protocols on commercial DNA synthesizers. In general, the synthesis of the oligonucleotide proceeds through a phosphorus-based intermediate. Such syntheses can be accomplished by one skilled in the art without undue experimentation.

Figure 5:
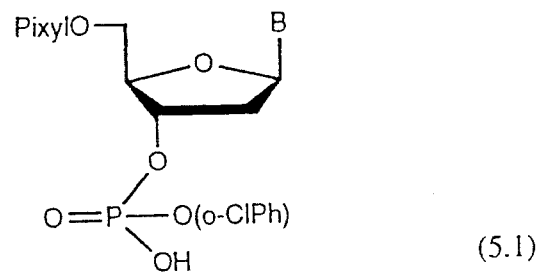
FIG. 5 shows potentially useful phosphonucleotide intermediates for use in constructing oligonucleotides of the present invention.
Figure 5:
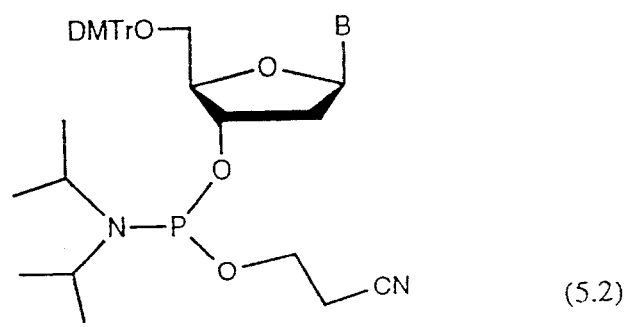
Figure 5:
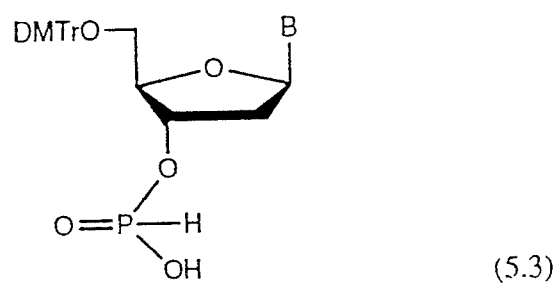
Figure 5:
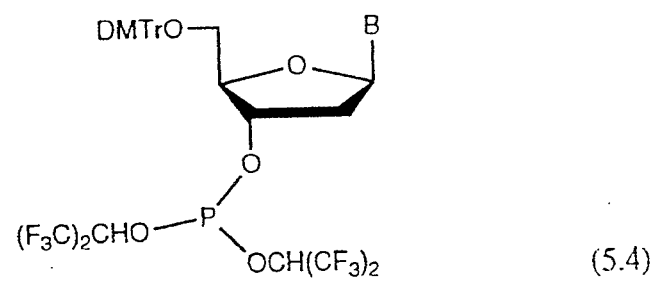

Examples of useful phosphorus-containing nucleotide intermediates are shown in FIG. 5 and include phosphotriesters according to Sproat and Gait (1984); phosphoramidites according to Beaucage and Caruthers (1981); H-phosphonates according to Froehler and Matteucci (1986); and phosphites according to Hasaka et al. (1991). The selection of an appropriate pathway to oligonucleotide synthesis may be selected by one skilled in the art without undue experimentation.

The synthesis of 3-nitropyrrole deoxyribonucleoside (1) and its protected phosphoramidite (2) is outlined in Scheme 1 below. The two reactants, 3-nitropyrrole and 2-deoxy-3,5-di-O-p-toluoyl-D-erythro-pentofuranosyl chloride are prepared by literature methods.

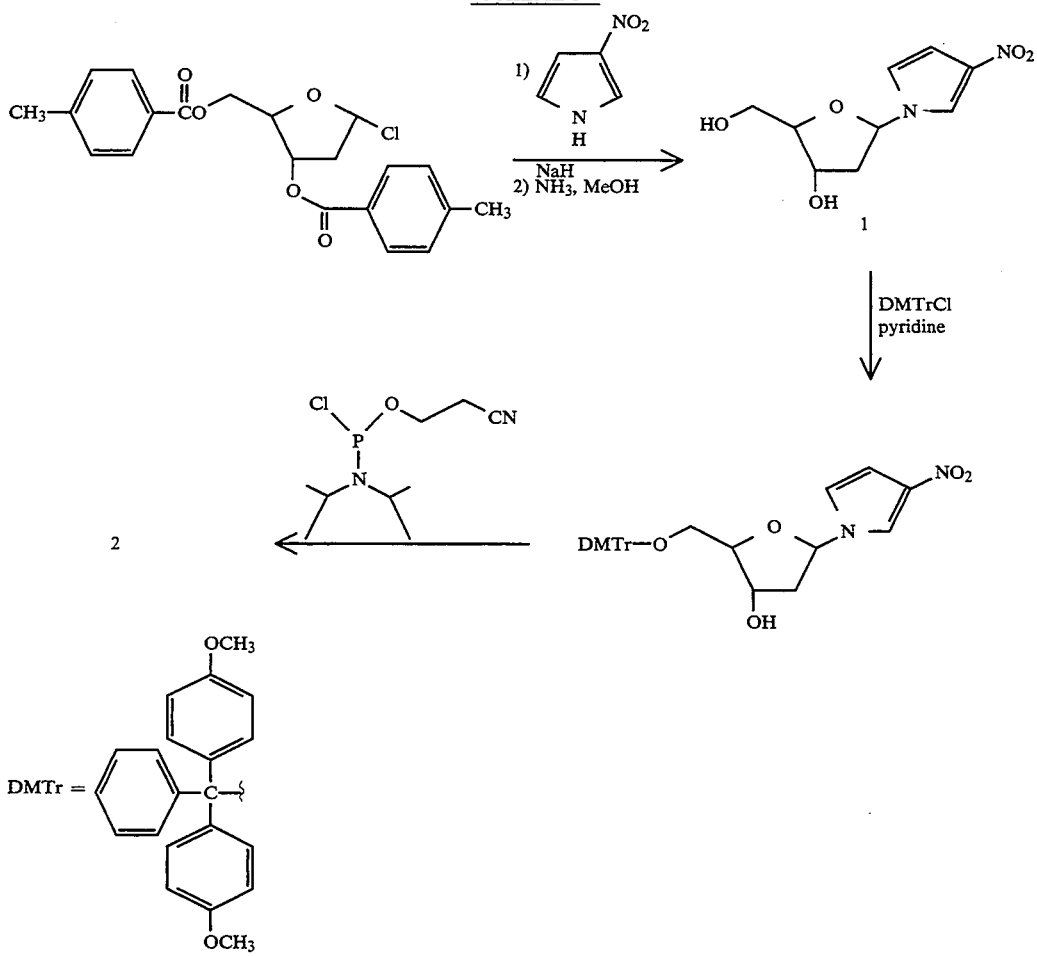

SCHEME 1

EXAMPLE 1

Modified nucleosides designed to function as universal nucleic acid bases were synthesized and their suitability as constituents of oligonucleotide probes were determined in physicochemical and molecular biological studies. As many as nine DNA bases of a 17-mer primer were replaced by 3-nitropyrrole deoxyribonucleoside without destroying the ability of the primer to initiate DNA synthesis.

The oligonucleotide sequences shown in Table 1 have been synthesized and tested as primers for DNA synthesis. The synthetic oligonucleotides were used as primers for sequencing single-stranded DNA by the Sanger method. Sanger dideoxy sequencing was performed using the United States Biochemical (USB) Sequenase version 2.0 sequencing kit. The DNA sequenced was a Hind III-Bluescript SK+subclone of a Drosophila neural peptide gene described in Nichols et al. J. Biol. Chem. 263: 12167 (1988). The template DNA was either ssDNA or dsDNA, and oligonucleotides were purified using 20% acrylamide-8M urea eletrophoretic gels and size exclusion chromatography. Approximately 1 μgDNA was sequenced with 0.1 μg oligonucleotide according to conditions provided by the supplier using $^{35}$S-dATP (Amersham). Aliquots of the sequencing reactions were electrophoresed on 6% acrylamide-8M urea sequencing gels after which the gel was dried and exposed to Kodak XAR X-ray film.

The results indicate that proper sequencing was achieved by oligonucleotides of the present invention. In particular, it was shown that as many as nine bases in a 17-mer sequence can be substituted by 3-nitropyrrole and a readable sequencing ladder obtained.

As previously skated, there are a variety of applications in addition to DNA sequencing for which the oligonucleotides of the present invention are particularly effective. For example, the use of such oligonucleotides in polymerase chain reaction (PCR) techniques would be extremely beneficial. PCR is a powerful technique with many applications such as, for example, the screening of individuals for medically significant mutations.

Also, the oligonucleotides of the present invention may be effective for hybridization uses such as the screening of complex DNA or genomic libraries, the quantification of nucleic acids and the analysis of a Northern or Southern blot. The use of a universal nucleoside at the degenerate sites would allow a single oligonucleotide to be used as a probe instead of a complex mixture.

It is also anticipated that the oligonucleotides of the present invention will find widespread applicability in both clinical and therapeutic settings. For example, DNA hybridization assays have become an important clinical tool for diagnosis of many disease states. Because of variations in the genetic sequence of virtually all pathogenic viruses, probes containing oligonucleotides having universal bases would be particularly effective. Therapeutic applications such as incorporation into triplex forming oligonucleotides and in antisense oligonucleotide therapeutics directed toward nucleic acid targets which have significant variability are also anticipated.

While the invention has been illustrated and described in detail in the foregoing description, the same is to be considered as illustrative and not restrictive in character, it being understood that only the preferred embodiment has been shown and described and that all changes and modifications that come within the spirit of the invention are desired to be protected.

TABLE 1

Modified Primers for Sanger Sequencing

| Primer No. | Sequence |
|---|---|
| 65 | 5'-CGT AAT CAG AAA ACA AT-3' |
| 66 | 5'-CGT AAN CAN AAN ACN AT-3' |
|  | (256 - degenerate primer mixture) |
| 67 | 5'-CGT AAI CAI AAI ACI AT-3' |
| 72 | 5'-CGT AAM CAM AAM ACM AT-3' |
| 73 | 5'-CGT AAT CAG AAA ACA MT-3' |
| 74 | 5'-CGT AAT CAG AAA ACA AT-3' |
|  | (synthesized on a universal support) |
| 75 | 5'-CGT AAT CAG AAA ACA AM-3' |

TABLE 1-continued

Modified Primers for Sanger Sequencing

| Primer No. | Sequence |
|---|---|
|  | (synthesized on a universal support) |
| 77 | 5'-CGT AAT CAG AAA MMM AT-3' |
| 78 | 5'-CGT AAT CAG MMM MMM AT-3' |
| 79 | 5'-CGT AAT CAG AAC ACA AT-3' |
| 81 | 5'-CGT AAT CAG AAA ACG AT-3' |
| 82 | 5'-CGT AAT CAG AAC ACG AT-3' |
| 83 | 5'-CGT AAT MMM MMM MMM AT-3' |
| 84 | 5'-CGT AAT CAG AAA ACA AC-3' |
| 85 | 5'-CGT AAC CAA AAC ACG AT-3' |

I = deoxyinosine
M = 3-nitropyrrole deoxyribonucleoside
All underlined bases are mismatches to target sequence.

We claim:
1. A nucleoside of the formula:

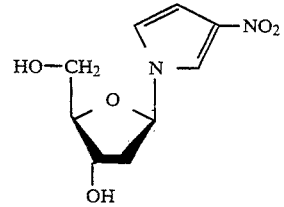

* * * * *

UNITED STATES PATENT AND TRADEMARK OFFICE
CERTIFICATE OF CORRECTION

PATENT NO. : 5,438,131

DATED : August 1, 1995

INVENTOR(S) : Donald E. Bergstrom et al.

It is certified that error appears in the above-identified patent and that said Letters Patent is hereby corrected as shown below:

In column 2, line 2, change "ally" to --any--;

In column 6, line 35, change "phosphide" to --phosphite--;

In column 6, line 14, change "polynucleohide" to --polynucleotide--;

In column 7, line 67, change "SM" to --8M--;

In column 8, line 45, change "skated" to --stated--.

In column 5, line 27, change "lit" to --It--.

Signed and Sealed this

Twenty-third Day of July, 1996

Attest:

BRUCE LEHMAN

Attesting Officer

Commissioner of Patents and Trademarks